(12) United States Patent
Villiers et al.

(10) Patent No.: US 8,083,797 B2
(45) Date of Patent: Dec. 27, 2011

(54) INTERVERTEBRAL PROSTHETIC DISC WITH SHOCK ABSORPTION

(75) Inventors: Malan de Villiers, Gauteng (ZA); David Hovda, Mountain View, CA (US); James Shapiro, San Francisco, CA (US)

(73) Assignee: SpinalMotion, Inc., Mountain View, CA (US)

( * ) Notice: Subject to any disclaimer, the term of this patent is extended or adjusted under 35 U.S.C. 154(b) by 1894 days.

(21) Appl. No.: 11/051,513

(22) Filed: Feb. 4, 2005

(65) Prior Publication Data

US 2006/0178744 A1  Aug. 10, 2006

(51) Int. Cl.
*A61F 2/44* (2006.01)

(52) U.S. Cl. .................................... 623/17.13

(58) Field of Classification Search ..... 623/17.11–17.16
See application file for complete search history.

(56) References Cited

U.S. PATENT DOCUMENTS

| | | |
|---|---|---|
| 3,486,505 A | 12/1969 | Morrison |
| 3,867,728 A | 2/1975 | Stubstad et al. |
| 4,309,777 A | 1/1982 | Patil |
| 4,531,917 A | 7/1985 | Linkow et al. |
| 4,566,466 A | 1/1986 | Ripple et al. |
| 4,619,660 A | 10/1986 | Christiansen et al. |
| 4,673,407 A | 6/1987 | Martin |
| 4,759,766 A | 7/1988 | Buettner-Janz et al. |
| 4,759,769 A | 7/1988 | Hedman et al. |
| 4,834,757 A | 5/1989 | Brantigan |
| 4,863,477 A | 9/1989 | Monson |
| 4,904,261 A | 2/1990 | Dove et al. |
| 4,917,704 A | 4/1990 | Frey et al. |
| 4,932,969 A | 6/1990 | Frey et al. |
| 4,946,378 A | 8/1990 | Hirayama et al. |
| 4,997,432 A | 3/1991 | Keller |
| 5,035,716 A | 7/1991 | Downey |
| 5,057,108 A | 10/1991 | Shetty et al. |
| 5,071,437 A | 12/1991 | Steffee |
| 5,122,130 A | 6/1992 | Keller |
| 5,195,526 A | 3/1993 | Michelson |
| 5,258,031 A | 11/1993 | Salib et al. |

(Continued)

FOREIGN PATENT DOCUMENTS

DE  3023353 A1  4/1981

(Continued)

OTHER PUBLICATIONS

Buttner-Janz, "The Development of the Artificial Disc," Introduction, pp. 1-18, Library of Congress Catalogue No. 92-75582, ISBN 0-9635430-0-8 (1989).

(Continued)

*Primary Examiner* — Nicholas Woodall
(74) *Attorney, Agent, or Firm* — Wilson Sonsini Goodrich & Rosati (57) ABSTRACT

A prosthetic disc for insertion between adjacent vertebrae includes upper and lower plates and a core having upper and lower curved surfaces disposed between the plates. At least one of the plates and/or the core includes a resilient material for absorbing shock or other forces applied by vertebrae. Optionally, resilient support members may be disposed within the resilient material to connect two portions of a plate or the core. Such support members may be springs, cylinders, wires or other resilient structures. The resilient material is held within the core or plate(s) via a surrounding retaining structure, such as a membrane. The resilient material disposed in one or more components of the prosthetic disc provides for shock absorption.

18 Claims, 4 Drawing Sheets

U.S. PATENT DOCUMENTS

| | | |
|---|---|---|
| 5,282,861 A | 2/1994 | Kaplan |
| 5,306,308 A | 4/1994 | Gross et al. |
| 5,314,477 A | 5/1994 | Marnay |
| 5,320,644 A | 6/1994 | Baumgartner |
| 5,370,697 A | 12/1994 | Baumgartner |
| 5,394,457 A | 2/1995 | Leibinger et al. |
| 5,401,269 A | 3/1995 | Buttner-Janz et al. |
| 5,415,704 A | 5/1995 | Davidson |
| 5,458,642 A | 10/1995 | Beer et al. |
| 5,462,575 A | 10/1995 | Del Corso |
| 5,484,437 A | 1/1996 | Michelson |
| 5,489,307 A | 2/1996 | Kuslich et al. |
| 5,505,732 A | 4/1996 | Michelson |
| 5,507,816 A | 4/1996 | Bullivant |
| 5,534,030 A | 7/1996 | Navarro et al. |
| 5,556,431 A | 9/1996 | Buttner-Janz |
| 5,674,296 A | 10/1997 | Bryan et al. |
| 5,676,701 A | 10/1997 | Yuan et al. |
| 5,676,702 A | 10/1997 | Ratron |
| 5,683,465 A | 11/1997 | Shinn et al. |
| 5,702,450 A | 12/1997 | Bisserie |
| 5,709,683 A | 1/1998 | Bagby |
| 5,728,159 A | 3/1998 | Stroever et al. |
| 5,741,253 A | 4/1998 | Michelson |
| 5,776,198 A | 7/1998 | Rabbe et al. |
| 5,782,832 A | 7/1998 | Larsen et al. |
| 5,797,909 A | 8/1998 | Michelson |
| 5,824,094 A | 10/1998 | Serhan et al. |
| 5,836,948 A | 11/1998 | Zucherman et al. |
| 5,865,846 A | 2/1999 | Bryan et al. |
| 5,865,848 A | 2/1999 | Baker |
| 5,888,226 A | 3/1999 | Rogozinski |
| 5,895,428 A | 4/1999 | Berry |
| 5,899,901 A | 5/1999 | Middleton |
| 5,899,911 A | 5/1999 | Carter |
| 5,928,284 A | 7/1999 | Mehdizadeh |
| 5,989,251 A | 11/1999 | Nichols |
| 5,989,291 A | 11/1999 | Ralph et al. |
| 6,001,130 A | 12/1999 | Bryan et al. |
| 6,019,792 A | 2/2000 | Cauthen |
| 6,022,376 A | 2/2000 | Assell et al. |
| 6,039,761 A | 3/2000 | Li et al. |
| 6,039,763 A | 3/2000 | Shelokov |
| 6,080,155 A | 6/2000 | Michelson |
| 6,083,228 A | 7/2000 | Michelson |
| 6,086,613 A | 7/2000 | Camino et al. |
| 6,096,038 A | 8/2000 | Michelson |
| 6,132,465 A | 10/2000 | Ray et al. |
| 6,136,031 A | 10/2000 | Middleton |
| 6,139,551 A | 10/2000 | Michelson et al. |
| 6,139,579 A | 10/2000 | Steffee et al. |
| 6,143,033 A | 11/2000 | Paul et al. |
| 6,146,421 A | 11/2000 | Gordon et al. |
| 6,156,067 A | 12/2000 | Bryan et al. |
| 6,159,214 A | 12/2000 | Michelson |
| 6,162,252 A | 12/2000 | Kuras et al. |
| 6,174,311 B1 | 1/2001 | Branch et al. |
| 6,176,881 B1 | 1/2001 | Schar et al. |
| 6,193,757 B1 | 2/2001 | Foley et al. |
| 6,224,595 B1 | 5/2001 | Michelson |
| 6,224,607 B1 | 5/2001 | Michelson |
| 6,231,609 B1 | 5/2001 | Mehdizadeh |
| 6,235,030 B1 | 5/2001 | Zucherman et al. |
| 6,261,296 B1 | 7/2001 | Aebi et al. |
| 6,264,695 B1 | 7/2001 | Stoy |
| 6,290,726 B1 | 9/2001 | Pope et al. |
| 6,296,664 B1 | 10/2001 | Middleton |
| 6,315,797 B1 | 11/2001 | Middleton |
| 6,322,567 B1 | 11/2001 | Mittelstadt et al. |
| 6,336,941 B1 | 1/2002 | Subba Rao et al. |
| 6,348,071 B1 | 2/2002 | Steffee et al. |
| 6,368,350 B1 | 4/2002 | Erickson et al. |
| 6,368,351 B1 | 4/2002 | Glenn et al. |
| 6,375,681 B1 | 4/2002 | Truscott |
| 6,375,682 B1 | 4/2002 | Fleischmann et al. |
| 6,395,032 B1 | 5/2002 | Gauchet |
| 6,402,785 B1 | 6/2002 | Zdeblick et al. |
| 6,409,766 B1 | 6/2002 | Brett |
| 6,413,278 B1 | 7/2002 | Marchosky |
| 6,416,551 B1 | 7/2002 | Keller |
| 6,436,098 B1 | 8/2002 | Michelson |
| 6,440,139 B2 | 8/2002 | Michelson |
| 6,447,544 B1 | 9/2002 | Michelson |
| 6,478,800 B1 | 11/2002 | Fraser et al. |
| 6,517,544 B1 | 2/2003 | Michelson |
| 6,517,580 B1 | 2/2003 | Ramadan et al. |
| 6,520,967 B1 | 2/2003 | Cauthen |
| 6,520,996 B1 | 2/2003 | Manasas et al. |
| 6,527,804 B1 | 3/2003 | Gauchet et al. |
| 6,533,817 B1 | 3/2003 | Norton et al. |
| 6,537,279 B1 | 3/2003 | Michelson |
| 6,554,863 B2 | 4/2003 | Paul et al. |
| 6,562,047 B2 | 5/2003 | Ralph et al. |
| 6,562,074 B2 | 5/2003 | Gerbec et al. |
| 6,565,574 B2 | 5/2003 | Michelson |
| 6,582,466 B1 | 6/2003 | Gauchet |
| 6,582,468 B1 | 6/2003 | Gauchet |
| 6,592,624 B1 | 7/2003 | Fraser et al. |
| 6,599,294 B2 | 7/2003 | Fuss et al. |
| 6,607,558 B2 | 8/2003 | Kuras |
| 6,607,559 B2 | 8/2003 | Ralph et al. |
| 6,610,092 B2 | 8/2003 | Ralph et al. |
| 6,623,525 B2 | 9/2003 | Ralph et al. |
| 6,645,248 B2 | 11/2003 | Casutt |
| 6,648,895 B2 | 11/2003 | Burkus et al. |
| 6,652,533 B2 | 11/2003 | O'Neil |
| 6,660,038 B2 | 12/2003 | Boyer, II et al. |
| 6,666,866 B2 | 12/2003 | Martz et al. |
| 6,669,731 B2 | 12/2003 | Ralph et al. |
| 6,669,732 B2 | 12/2003 | Serhan et al. |
| 6,673,113 B2 | 1/2004 | Ralph et al. |
| 6,682,562 B2 | 1/2004 | Viart et al. |
| 6,689,132 B2 | 2/2004 | Biscup |
| 6,706,068 B2 | 3/2004 | Ferree |
| 6,709,439 B2 | 3/2004 | Rogers et al. |
| 6,712,819 B2 | 3/2004 | Zucherman et al. |
| 6,712,825 B2 | 3/2004 | Aebi et al. |
| 6,719,794 B2 | 4/2004 | Gerber et al. |
| 6,723,097 B2 | 4/2004 | Fraser et al. |
| 6,726,720 B2 | 4/2004 | Ross et al. |
| 6,726,721 B2 | 4/2004 | Stoy et al. |
| 6,733,532 B1 | 5/2004 | Gauchet et al. |
| 6,740,118 B2 | 5/2004 | Eisermann et al. |
| 6,740,119 B2 | 5/2004 | Ralph et al. |
| 6,752,832 B2 | 6/2004 | Neumann |
| 6,755,841 B2 | 6/2004 | Fraser et al. |
| 6,764,512 B2 | 7/2004 | Keller |
| 6,764,515 B2 | 7/2004 | Ralph et al. |
| 6,770,095 B2 | 8/2004 | Grinberg et al. |
| 6,790,233 B2 | 9/2004 | Brodke et al. |
| 6,793,678 B2 | 9/2004 | Hawkins |
| 6,814,737 B2 | 11/2004 | Cauthan |
| 6,821,298 B1 | 11/2004 | Jackson |
| 6,827,740 B1 | 12/2004 | Michelson |
| 6,830,570 B1 | 12/2004 | Frey et al. |
| 6,846,328 B2 | 1/2005 | Cauthen |
| 6,852,126 B2 | 2/2005 | Ahlgren |
| 6,863,673 B2 | 3/2005 | Gerbec et al. |
| 6,875,213 B2 | 4/2005 | Michelson |
| 6,896,680 B2 | 5/2005 | Michelson |
| 6,899,735 B2 | 5/2005 | Coates et al. |
| 6,936,071 B1 | 8/2005 | Marnay et al. |
| 6,936,132 B2 | 8/2005 | Topolnitsky |
| 6,964,686 B2 | 11/2005 | Gordon |
| 6,966,929 B2 | 11/2005 | Mitchell |
| 6,966,931 B2 * | 11/2005 | Huang ............ 623/17.16 |
| 6,986,788 B2 | 1/2006 | Paul et al. |
| 6,989,011 B2 | 1/2006 | Paul et al. |
| 6,994,727 B2 | 2/2006 | Khandkar et al. |
| 7,011,684 B2 | 3/2006 | Eckman |
| 7,022,138 B2 | 4/2006 | Mashburn |
| 7,025,787 B2 | 4/2006 | Bryan et al. |
| 7,044,983 B1 | 5/2006 | Cheng |
| 7,056,344 B2 | 6/2006 | Huppert et al. |
| 7,060,073 B2 | 6/2006 | Frey et al. |
| 7,066,958 B2 | 6/2006 | Ferree |
| 7,081,120 B2 | 7/2006 | Li et al. |

| Patent/Publication | Date | Name |
|---|---|---|
| 7,083,651 B2 | 8/2006 | Diaz et al. |
| 7,087,055 B2 | 8/2006 | Lim et al. |
| 7,097,648 B1 | 8/2006 | Globerman et al. |
| 7,115,132 B2 | 10/2006 | Errico et al. |
| 7,118,580 B1 | 10/2006 | Beyersdorff et al. |
| 7,147,665 B1 | 12/2006 | Bryan et al. |
| 7,153,325 B2 | 12/2006 | Kim et al. |
| 7,169,182 B2 | 1/2007 | Errico et al. |
| 7,179,294 B2 | 2/2007 | Eisermann et al. |
| 7,182,784 B2 | 2/2007 | Evans et al. |
| 7,198,644 B2 | 4/2007 | Schultz et al. |
| 7,207,991 B2 | 4/2007 | Michelson |
| 7,214,244 B2 | 5/2007 | Zubok et al. |
| 7,217,291 B2 | 5/2007 | Zucherman et al. |
| 7,235,082 B2 | 6/2007 | Bartish et al. |
| 7,235,103 B2 | 6/2007 | Rivin |
| 7,250,060 B2 | 7/2007 | Trieu |
| 7,255,714 B2 | 8/2007 | Malek |
| 7,261,739 B2 | 8/2007 | Ralph et al. |
| 7,267,688 B2 | 9/2007 | Ferree |
| 7,270,679 B2 | 9/2007 | Istephanous et al. |
| 7,270,682 B2 | 9/2007 | Frigg et al. |
| 7,303,582 B2 | 12/2007 | Brady |
| 7,303,583 B1 | 12/2007 | Schar et al. |
| 7,318,839 B2 | 1/2008 | Malberg et al. |
| 7,326,250 B2 | 2/2008 | Beaurain et al. |
| 7,331,995 B2 | 2/2008 | Eisermann et al. |
| 7,429,270 B2 | 9/2008 | Baumgartner et al. |
| 7,442,211 B2 | 10/2008 | de Villiers et al. |
| 7,452,380 B2 | 11/2008 | Zubok et al. |
| 7,491,241 B2 | 2/2009 | Errico et al. |
| 7,494,508 B2 | 2/2009 | Zeegers |
| 7,517,363 B2 * | 4/2009 | Rogers et al. ............. 623/17.11 |
| 7,549,995 B2 | 6/2009 | Schultz et al. |
| 7,563,284 B2 | 7/2009 | Coppes et al. |
| 7,563,286 B2 * | 7/2009 | Gerber et al. ............. 623/17.14 |
| 7,708,776 B1 | 5/2010 | Blain et al. |
| 7,708,777 B2 | 5/2010 | O'Neil et al. |
| 7,731,753 B2 * | 6/2010 | Reo et al. .................. 623/17.13 |
| 7,731,754 B2 | 6/2010 | de Villiers et al. |
| 2001/0016773 A1 | 8/2001 | Serhan et al. |
| 2001/0029377 A1 | 10/2001 | Aebi et al. |
| 2002/0022845 A1 | 2/2002 | Zdeblick et al. |
| 2002/0035400 A1 | 3/2002 | Bryan et al. |
| 2002/0045904 A1 | 4/2002 | Fuss et al. |
| 2002/0068936 A1 | 6/2002 | Burkus et al. |
| 2002/0091392 A1 | 7/2002 | Michelson |
| 2002/0116009 A1 | 8/2002 | Fraser et al. |
| 2002/0123753 A1 | 9/2002 | Michelson |
| 2002/0128715 A1 | 9/2002 | Bryan et al. |
| 2002/0165550 A1 | 11/2002 | Frey et al. |
| 2002/0177897 A1 | 11/2002 | Michelson |
| 2002/0198532 A1 | 12/2002 | Michelson |
| 2003/0009224 A1 | 1/2003 | Kuras |
| 2003/0023245 A1 | 1/2003 | Ralph et al. |
| 2003/0028249 A1 | 2/2003 | Baccelli et al. |
| 2003/0040746 A1 | 2/2003 | Mitchell et al. |
| 2003/0045884 A1 | 3/2003 | Robie et al. |
| 2003/0045939 A1 | 3/2003 | Casutt |
| 2003/0074076 A1 | 4/2003 | Ferree |
| 2003/0083747 A1 | 5/2003 | Winterbottom et al. |
| 2003/0100951 A1 | 5/2003 | Serhan et al. |
| 2003/0125739 A1 | 7/2003 | Bagga |
| 2003/0130662 A1 | 7/2003 | Michelson |
| 2003/0135277 A1 | 7/2003 | Bryan et al. |
| 2003/0139812 A1 | 7/2003 | Garcia et al. |
| 2003/0187448 A1 | 10/2003 | Michelson |
| 2003/0191536 A1 | 10/2003 | Ferree |
| 2003/0195517 A1 | 10/2003 | Michelson |
| 2003/0195631 A1 | 10/2003 | Ferree |
| 2003/0199982 A1 | 10/2003 | Bryan |
| 2003/0204261 A1 | 10/2003 | Eisermann et al. |
| 2003/0208271 A1 | 11/2003 | Kuras |
| 2003/0229358 A1 | 12/2003 | Errico et al. |
| 2003/0233145 A1 | 12/2003 | Landry et al. |
| 2004/0002761 A1 | 1/2004 | Rogers et al. |
| 2004/0024407 A1 | 2/2004 | Ralph |
| 2004/0024410 A1 | 2/2004 | Olson et al. |
| 2004/0030391 A1 | 2/2004 | Ferree |
| 2004/0034426 A1 | 2/2004 | Errico et al. |
| 2004/0054411 A1 | 3/2004 | Kelly et al. |
| 2004/0059318 A1 | 3/2004 | Zhang et al. |
| 2004/0073307 A1 | 4/2004 | Keller |
| 2004/0073311 A1 | 4/2004 | Ferree |
| 2004/0073312 A1 | 4/2004 | Eisermann et al. |
| 2004/0093087 A1 | 5/2004 | Ferree et al. |
| 2004/0097928 A1 | 5/2004 | Zdeblick et al. |
| 2004/0098131 A1 | 5/2004 | Bryan et al. |
| 2004/0111155 A1 * | 6/2004 | Ferree ......................... 623/17.13 |
| 2004/0117021 A1 | 6/2004 | Biedermann et al. |
| 2004/0143270 A1 | 7/2004 | Zuckerman et al. |
| 2004/0143332 A1 | 7/2004 | Krueger et al. |
| 2004/0143334 A1 | 7/2004 | Ferree |
| 2004/0167626 A1 | 8/2004 | Geremakis et al. |
| 2004/0176843 A1 | 9/2004 | Zubok et al. |
| 2004/0186569 A1 | 9/2004 | Berry |
| 2004/0215342 A1 * | 10/2004 | Suddaby .................... 623/17.12 |
| 2004/0225295 A1 | 11/2004 | Zubok et al. |
| 2004/0225365 A1 | 11/2004 | Eisermann et al. |
| 2004/0236426 A1 | 11/2004 | Ralph et al. |
| 2004/0243238 A1 * | 12/2004 | Arnin et al. ................ 623/17.12 |
| 2004/0254644 A1 | 12/2004 | Taylor |
| 2005/0015094 A1 | 1/2005 | Keller |
| 2005/0015095 A1 | 1/2005 | Keller |
| 2005/0015152 A1 | 1/2005 | Sweeney |
| 2005/0021145 A1 | 1/2005 | de Villiers et al. |
| 2005/0021146 A1 | 1/2005 | de Villiers et al. |
| 2005/0027360 A1 | 2/2005 | Webb et al. |
| 2005/0038515 A1 | 2/2005 | Kunzler |
| 2005/0043800 A1 | 2/2005 | Paul et al. |
| 2005/0085917 A1 | 4/2005 | Marnay et al. |
| 2005/0107881 A1 | 5/2005 | Alleyne et al. |
| 2005/0113842 A1 | 5/2005 | Bertagnoli et al. |
| 2005/0113928 A1 | 5/2005 | Cragg |
| 2005/0143824 A1 | 6/2005 | Richelsoph et al. |
| 2005/0149189 A1 | 7/2005 | Mokhtar et al. |
| 2005/0154463 A1 | 7/2005 | Trieu |
| 2005/0165408 A1 | 7/2005 | Puno et al. |
| 2005/0165485 A1 * | 7/2005 | Trieu ......................... 623/17.13 |
| 2005/0171604 A1 | 8/2005 | Michalow |
| 2005/0192586 A1 | 9/2005 | Zuckerman et al. |
| 2005/0192670 A1 | 9/2005 | Zubok et al. |
| 2005/0197706 A1 | 9/2005 | Hovorka et al. |
| 2005/0216081 A1 | 9/2005 | Taylor |
| 2005/0216084 A1 | 9/2005 | Fleischmann et al. |
| 2005/0234553 A1 | 10/2005 | Gordon |
| 2005/0251260 A1 | 11/2005 | Gerber et al. |
| 2005/0251261 A1 | 11/2005 | Peterman |
| 2005/0251262 A1 | 11/2005 | de Villiers et al. |
| 2005/0261772 A1 | 11/2005 | Filippi et al. |
| 2005/0267580 A1 | 12/2005 | Suddaby |
| 2005/0267581 A1 | 12/2005 | Marnay et al. |
| 2006/0004377 A1 | 1/2006 | Keller |
| 2006/0004453 A1 | 1/2006 | Bartish et al. |
| 2006/0015183 A1 | 1/2006 | Gilbert et al. |
| 2006/0020342 A1 | 1/2006 | Ferree et al. |
| 2006/0025862 A1 | 2/2006 | de Villiers et al. |
| 2006/0029186 A1 | 2/2006 | de Villiers et al. |
| 2006/0030857 A1 | 2/2006 | de Villiers et al. |
| 2006/0030862 A1 | 2/2006 | de Villiers et al. |
| 2006/0036325 A1 | 2/2006 | Paul et al. |
| 2006/0041313 A1 | 2/2006 | Allard et al. |
| 2006/0041314 A1 | 2/2006 | Millard |
| 2006/0052870 A1 | 3/2006 | Feree |
| 2006/0064169 A1 * | 3/2006 | Ferree ......................... 623/17.12 |
| 2006/0069439 A1 | 3/2006 | Zucherman et al. |
| 2006/0116768 A1 | 6/2006 | Krueger et al. |
| 2006/0142858 A1 | 6/2006 | Colleran |
| 2006/0142862 A1 | 6/2006 | Diaz et al. |
| 2006/0155378 A1 | 7/2006 | Eckman |
| 2006/0167549 A1 | 7/2006 | Mathys et al. |
| 2006/0178746 A1 | 8/2006 | Bartish, Jr. et al. |
| 2006/0195097 A1 | 8/2006 | Evans et al. |
| 2006/0200239 A1 | 9/2006 | Rothman et al. |
| 2006/0224241 A1 | 10/2006 | Butler et al. |
| 2006/0235426 A1 | 10/2006 | Lim et al. |
| 2006/0235525 A1 | 10/2006 | Gil et al. |
| 2006/0235527 A1 | 10/2006 | Buettner-Janz et al. |

| | | | |
|---|---|---|---|
| 2006/0241641 A1 | 10/2006 | Albans et al. | |
| 2006/0241766 A1 | 10/2006 | Felton et al. | |
| 2006/0259144 A1 | 11/2006 | Trieu | |
| 2006/0259146 A1 | 11/2006 | Navarro et al. | |
| 2006/0265068 A1 | 11/2006 | Schwab | |
| 2006/0265077 A1 | 11/2006 | Zwirkoski | |
| 2006/0287728 A1 | 12/2006 | Mokhtar et al. | |
| 2006/0293752 A1 | 12/2006 | Moumene et al. | |
| 2006/0293753 A1* | 12/2006 | Thramann | 623/17.13 |
| 2006/0293754 A1 | 12/2006 | de Villiers et al. | |
| 2007/0010826 A1 | 1/2007 | Rhoda et al. | |
| 2007/0021837 A1 | 1/2007 | Ashman et al. | |
| 2007/0032875 A1 | 2/2007 | Blacklock et al. | |
| 2007/0061011 A1 | 3/2007 | de Villiers et al. | |
| 2007/0067035 A1 | 3/2007 | Falahee | |
| 2007/0067036 A1 | 3/2007 | Hudgins et al. | |
| 2007/0073398 A1 | 3/2007 | Fabian et al. | |
| 2007/0093898 A1 | 4/2007 | Schwab et al. | |
| 2007/0100453 A1 | 5/2007 | Parsons et al. | |
| 2007/0100454 A1 | 5/2007 | Burgess et al. | |
| 2007/0100456 A1 | 5/2007 | Dooris et al. | |
| 2007/0123903 A1 | 5/2007 | Raymond et al. | |
| 2007/0123904 A1 | 5/2007 | Stad et al. | |
| 2007/0135923 A1 | 6/2007 | Peterman et al. | |
| 2007/0162133 A1 | 7/2007 | Doubler et al. | |
| 2007/0168033 A1 | 7/2007 | Kim et al. | |
| 2007/0168036 A1 | 7/2007 | Ainsworth et al. | |
| 2007/0179615 A1 | 8/2007 | Heinz et al. | |
| 2007/0213821 A1 | 9/2007 | Kwak et al. | |
| 2007/0233077 A1 | 10/2007 | Khalili | |
| 2007/0233247 A1 | 10/2007 | Schwab | |
| 2007/0233248 A1 | 10/2007 | Schwab et al. | |
| 2007/0233251 A1 | 10/2007 | Abdou | |
| 2007/0270970 A1 | 11/2007 | Trieu | |
| 2007/0282449 A1 | 12/2007 | de Villiers et al. | |
| 2007/0299521 A1 | 12/2007 | Glenn et al. | |
| 2008/0015698 A1 | 1/2008 | Marino et al. | |
| 2008/0015701 A1 | 1/2008 | Garcia et al. | |
| 2008/0021557 A1 | 1/2008 | Trieu | |
| 2008/0051900 A1 | 2/2008 | de Villiers et al. | |
| 2008/0051901 A1 | 2/2008 | de Villiers et al. | |
| 2008/0125864 A1 | 5/2008 | de Villiers et al. | |
| 2008/0125865 A1 | 5/2008 | Abdelgany | |
| 2008/0133011 A1 | 6/2008 | de Villiers et al. | |
| 2008/0154301 A1 | 6/2008 | de Villiers et al. | |
| 2008/0154382 A1 | 6/2008 | de Villiers et al. | |
| 2008/0215155 A1 | 9/2008 | de Villiers et al. | |
| 2008/0221696 A1 | 9/2008 | de Villiers et al. | |
| 2008/0228274 A1 | 9/2008 | de Villiers et al. | |
| 2008/0228277 A1 | 9/2008 | de Villiers et al. | |
| 2008/0294259 A1 | 11/2008 | de Villiers et al. | |
| 2009/0043391 A1 | 2/2009 | de Villiers et al. | |
| 2009/0048674 A1 | 2/2009 | Zubok et al. | |
| 2009/0048677 A1 | 2/2009 | McLeod et al. | |
| 2009/0076614 A1 | 3/2009 | Arramon | |
| 2009/0192617 A1 | 7/2009 | Arramon et al. | |
| 2009/0205188 A1 | 8/2009 | de Villiers et al. | |
| 2009/0210060 A1 | 8/2009 | de Villiers et al. | |
| 2009/0222101 A1 | 9/2009 | de Villiers et al. | |
| 2009/0276051 A1 | 11/2009 | Arramon et al. | |
| 2009/0326656 A1 | 12/2009 | de Villiers et al. | |
| 2010/0004746 A1 | 1/2010 | Arramon | |
| 2010/0016972 A1 | 1/2010 | Jansen et al. | |
| 2010/0016973 A1 | 1/2010 | de Villiers et al. | |
| 2010/0030335 A1 | 2/2010 | Arramon | |
| 2010/0049040 A1 | 2/2010 | de Villiers et al. | |
| 2010/0069976 A1 | 3/2010 | de Villiers et al. | |
| 2010/0076558 A1 | 3/2010 | de Villiers et al. | |
| 2010/0087868 A1 | 4/2010 | Barr et al. | |
| 2010/0179419 A1 | 7/2010 | de Villiers et al. | |

FOREIGN PATENT DOCUMENTS

| | | |
|---|---|---|
| DE | 10035182 A1 | 7/2002 |
| EP | 0 333 990 A2 | 9/1989 |
| EP | 0333990 A2 | 9/1989 |
| EP | 0 560 140 A1 | 9/1993 |
| EP | 0 560 141 A1 | 9/1993 |
| EP | 0560140 A1 | 9/1993 |
| EP | 0560141 A1 | 9/1993 |
| EP | 0 591 712 A1 | 4/1994 |
| EP | 0 820 740 | 1/1998 |
| EP | 1 142 544 A1 | 10/2001 |
| EP | 1142544 A1 | 10/2001 |
| EP | 1 153 582 A2 | 11/2001 |
| EP | 1153582 A3 | 11/2001 |
| EP | 1 250 898 A1 | 10/2002 |
| EP | 1250898 A1 | 10/2002 |
| EP | 1 306 064 A1 | 5/2003 |
| EP | 1306064 A1 | 5/2003 |
| EP | 1 344 493 A1 | 9/2003 |
| EP | 1 344 506 A1 | 9/2003 |
| EP | 1 344 507 A2 | 9/2003 |
| EP | 1 344 508 A3 | 9/2003 |
| EP | 1344493 A1 | 9/2003 |
| EP | 1344506 A1 | 9/2003 |
| EP | 1344507 A1 | 9/2003 |
| EP | 1344508 A1 | 9/2003 |
| EP | 1 417 940 A1 | 5/2004 |
| EP | 1417940 A1 | 5/2004 |
| EP | 1 570 813 | 9/2005 |
| FR | 2 803 741 | 7/2001 |
| JP | 61-122859 | 6/1986 |
| JP | 63-164948 | 7/1988 |
| WO | WO 99/20209 | 4/1999 |
| WO | WO 99/30651 | 6/1999 |
| WO | WO 00/04851 | 2/2000 |
| WO | WO 00/35384 | 6/2000 |
| WO | WO 00/42954 | 7/2000 |
| WO | WO 00/42954 A3 | 11/2000 |
| WO | WO 01/01893 A1 | 1/2001 |
| WO | WO 01/15637 | 3/2001 |
| WO | WO 01/68003 A1 | 9/2001 |
| WO | WO 02/11650 | 2/2002 |
| WO | WO 04/000170 | 12/2003 |
| WO | WO 04/000171 | 12/2003 |
| WO | 2004026187 A1 | 4/2004 |
| WO | WO 2004/026187 A1 | 4/2004 |
| WO | WO 2004/054477 | 7/2004 |
| WO | WO 2005/004756 A2 | 1/2005 |
| WO | WO 2005/004756 A3 | 1/2005 |
| WO | 2005053580 A1 | 6/2005 |
| WO | WO 2005/053580 A1 | 6/2005 |
| WO | WO 2005/072662 | 8/2005 |
| WO | WO 2005/112834 | 12/2005 |
| WO | WO 2005/112834 A3 | 5/2006 |
| WO | WO 2006/119092 A2 | 11/2006 |
| WO | WO 2006/119092 A3 | 11/2006 |
| WO | WO 2007/121320 | 10/2007 |
| ZA | 03/9312 | 11/2003 |

OTHER PUBLICATIONS

Hellier et al., "Wear Studies for Development of an Intervertebral Disc Prosthesis," *Spine*, vol. 17 No. 6 Supplement pp. 86-96 (1992).

Lee et al., "Impact Response of the Intervertebral Disc in a Finite-Element Model," *Spine* vol. 25, No. 19, pp. 2431-2439.

Lehuec et al., "Shock Absorption in Lumber Disc Prosthesis," *Journal of Spinal Disorders & Techniques*, vol. 16, No. 4, pp. 346-351.

Hellier, et al., "Wear Studies for Development of an Intervertebral Disc Prosthesis," Spine, (1992) vol. 17 (6), Supplement pp. 86-96.

Karin Buttner-Janz, The Development of the Artificial Disc, Introduction, 1989, pp. 1-18, Library of Congress Catalogue No. 92-75582, ISBN 0-9635430-0-8.

PCT International Search Report.

* cited by examiner

INTERVERTEBRAL PROSTHETIC DISC WITH SHOCK ABSORPTION

CROSS-REFERENCES TO RELATED APPLICATIONS

This application is related to U.S. patent application Ser. Nos. 10/855,253 and 10/855,817, both of which were filed on May 26, 2004, and 10/903,913, filed Jul. 30, 2004. All of the aforementioned references are hereby incorporated fully by reference.

BACKGROUND OF THE INVENTION

This invention relates to medical devices and methods. More specifically, the invention relates to intervertebral disc prostheses.

Back pain takes an enormous toll on the health and productivity of people around the world. According to the American Academy of Orthopedic Surgeons, approximately 80 percent of Americans will experience back pain at some time in their life. In just the year 2000, approximately 26 million visits were made to physicians' offices due to back problems in the United States. On any one day, it is estimated that 5% of the working population in America is disabled by back pain.

One common cause of back pain is injury, degeneration and/or dysfunction of one or more intervertebral discs. Intervertebral discs are the soft tissue structures located between each of the thirty-three vertebral bones that make up the vertebral (spinal) column. Essentially, the discs allow the vertebrae to move relative to one another. The vertebral column and discs are vital anatomical structures, in that they form a central axis that supports the head and torso, allow for movement of the back, and protect the spinal cord, which passes through the vertebrae in proximity to the discs.

Discs often become damaged due to wear and tear or acute injury. For example, discs may bulge (herniate), tear, rupture, degenerate or the like. A bulging disc may press against the spinal cord or a nerve exiting the spinal cord, causing "radicular" pain (pain in one or more extremities caused by impingement of a nerve root). Degeneration or other damage to a disc may cause a loss of "disc height," meaning that the natural space between two vertebrae decreases. Decreased disc height may cause a disc to bulge, facet loads to increase, two vertebrae to rub together in an unnatural way and/or increased pressure on certain parts of the vertebrae and/or nerve roots, thus causing pain. In general, chronic and acute damage to intervertebral discs is a common source of back related pain and loss of mobility.

When one or more damaged intervertebral discs cause a patient pain and discomfort, surgery is often required. Traditionally, surgical procedures for treating intervertebral discs have involved discectomy (partial or total removal of a disc), with or without fusion of the two vertebrae adjacent to the disc. Fusion of the two vertebrae is achieved by inserting bone graft material between the two vertebrae such that the two vertebrae and the graft material grow together. Oftentimes, pins, rods, screws, cages and/or the like are inserted between the vertebrae to act as support structures to hold the vertebrae and graft material in place while they permanently fuse together. Although fusion often treats the back pain, it reduces the patient's ability to move, because the back cannot bend or twist at the fused area. In addition, fusion increases stresses at adjacent levels of the spine, potentially accelerating degeneration of these discs.

In an attempt to treat disc related pain without fusion, an alternative approach has been developed, in which a movable, implantable, artificial intervertebral disc (or "disc prosthesis") is inserted between two vertebrae. A number of different intervertebral disc prostheses are currently being developed. For example, the inventors of the present invention have developed disc prostheses described in U.S. patent application Ser. Nos. 10/855,817 and 10/855,253, previously incorporated by reference. Other examples of intervertebral disc prostheses are the LINK® SB Charitédisc (provided by DePuy Spine, Inc.) Mobidisk® (provided by LDR Medical (www.ldrmedical.fr)), the Bryan Cervical Disc (provided by Medtronic Sofamor Danek, Inc.), the ProDisc® or ProDisc-C® (from Synthes Stratec, Inc.), and the PCM disc (provided by Cervitech, Inc.). Although existing disc prostheses provide advantages over traditional treatment methods, improvements are ongoing.

Figure 1:
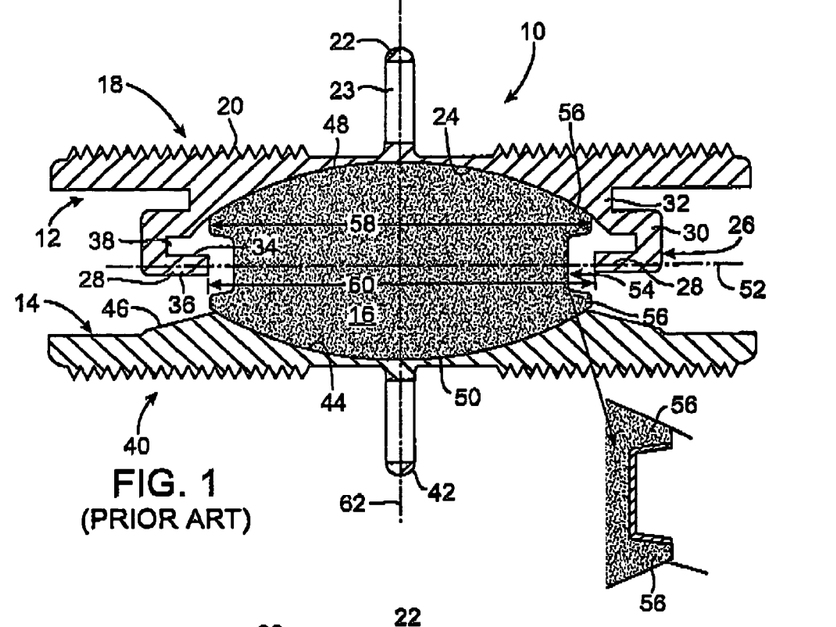
FIG. 1 is a cross-sectional anterior view of an intervertebral disc prosthesis with the prosthesis plates and core in vertical alignment, according to one embodiment of the present invention.
Figure 2:
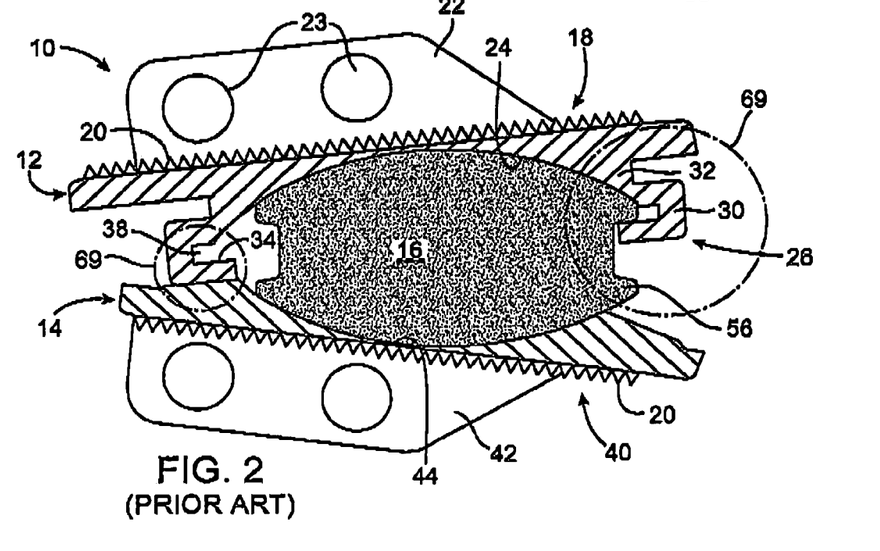
FIG. 2 is a side view of the prosthetic disc in FIG. 1 after sliding movement of the plates over the core.

One type of intervertebral disc prosthesis generally includes upper and lower prosthesis plates or shells, which locate against and engage the adjacent vertebral bodies, and a low friction core between the plates. For example, one intervertebral disc prosthesis design is shown in FIGS. 1 and 2 and is described fully in U.S. patent application Ser. No. 10/855,253, which was previously incorporated by reference. In some designs, the core has upper and lower convexly curved surfaces, and the plates have corresponding, concavely curved recesses which cooperate with the curved surfaces of the core. This allows the plates to slide over the core to allow required spinal movements to take place. Some type of movement limiting structure is provided, to prevent the core from slipping out between the plates. Typically, the plates are made of one or more metals, and the core is made of a polymeric substance.

A number of improvements in intervertebral disc prostheses have already been made. For example, a disc with a partially or completely metallic core for reducing wear and tear of the core is described in U.S. patent application Ser. No. 10/903,913, which was previously incorporated by reference. Additional improvements are continually being sought. For example, currently available intervertebral prostheses do not provide for cushioning or shock absorption, which would help absorb forced applied to the prostheses from the vertebrae to which they are attached.

Therefore, a need exists for improved intervertebral disc prostheses. Ideally, such improved prostheses would provide for shock absorption of forces applied to it by vertebrae.

BRIEF SUMMARY OF THE INVENTION

In one aspect of the present invention, an intervertebral disc prosthesis comprises a core having upper and lower curved surfaces and upper and lower plates disposed about the core. Each plate, in turn, comprises an outer surface which engages a vertebra and an inner curved surface shaped to slide over one of the curved surfaces of the core. Furthermore, at least one of the upper and lower plates includes at least one resilient material disposed between the outer and inner surfaces. In some embodiments, each of the upper and lower plates includes at least one resilient material disposed between its outer and inner surfaces. Any suitable resilient material may be used, such as but not limited to a polymer, hydrogel or the like. In various embodiments, the resilient material may be a liquid, semi-solid, gel, solid material or multiple layers of solid material.

In some embodiments, the resilient material is disposed in one or more layers between the inner and outer surfaces. Such embodiments may optionally include at least one retaining member disposed between the outer and inner surfaces and around the resilient material, to retain the resilient material between the outer and inner surfaces. For example, the retaining member may include a membrane, such as non-porous membrane, a mesh or the like. In some embodiments, the membrane comprises a polymer. Optionally, the prosthesis may further include at least one resilient support member disposed within the layer(s) of material and attached to the inner and outer surfaces of each plate. For example, such resilient support members may comprise a plurality of springs, cylinders, wires or the like. In one embodiment, each of the springs is surrounded by a first cylinder extending from the outer surface and a second cylinder extending from the inner surface, and one of the first and second cylinders has an outer diameter sized to fit within the inner diameter of the other cylinder, to allow the smaller cylinder to move in and out of the larger cylinder with the movement of the spring. An alternative embodiment includes first cylinder extending from the outer surface, a second cylinder extending from the inner surface and at least partially extending into the first cylinder, wherein the first and second cylinders are slidably movable relative to one another; and locking mechanisms on the first and second cylinders for limiting their movement relative to one another to prevent their separation.

Various embodiments of an intervertebral disc prosthesis may have a number of different design variations in order to provide either more or less shock absorption. For example, one embodiment may have a thicker or taller endplate to allow for more resilient material within the endplate than an endplate of another embodiment. The density of the resilient material may also be selected to confer different levels of shock absorption. Similarly, the stiffness of resilient support members, such as springs or cylinders, may be selected to confer different levels of shock absorption. Thus, any of a number of variables may be adjusted to give a disc prosthesis a desired amount of shock absorption. Such variability may be useful, for example, in making different disc prostheses for use in the cervical spine versus the lumbar spine, where a stiffer prosthesis may be desirable.

In some embodiments, the outer surface of at least one plate includes a retaining ring, and the inner surface of the plate is fitted within the retaining ring. In such embodiments, the outer surface may be heated, the inner surface may be positioned within the retaining ring, and the outer surface may be allowed to cool and shrink, thus retaining the inner surface within the retaining ring. Such a method of making a prosthesis is described further below.

In some embodiments, the core is made of a polymer, a ceramic, a metal or some combination thereof. For example, metals may include cobalt chrome molybdenum, titanium, stainless steel or the like. In some embodiments, the resilient material is further disposed between the upper and lower curved surfaces of the core. Optionally, the prosthesis may further include at least one resilient support member disposed within the resilient material and attached to the upper and lower curved surfaces. Any suitable resilient support structure may be used, such as springs, cylinders, wires or the like, as described above.

Any of a number of suitable materials may be used to construct the outer and inner surfaces of the plates, such as ceramic material or one or more metals selected from the group consisting of cobalt chrome molybdenum, titanium and stainless steel. In some embodiments, the outer surface of the plate is made of one material, such as a metal, and the inner surface of the plate is made of a different material, such as a different metal or a ceramic material. In some embodiments, the core and outer and inner surfaces comprise the same metal. In some embodiments, the prosthesis further includes a restraining structure on at least one of the upper plate, the lower plate and the core to hold the core against a curved surface of at least one of the plates during sliding movement of the plates over the core. For example, the restraining structure may comprise a peripheral restraining structure. In a typical embodiment, movement of the core within the restraining structure is unconstrained.

Optionally, the outer surfaces of the upper and lower plates may have at least one surface feature for promoting attachment of the outer surfaces to the vertebrae. For example, the surface feature(s) may include a plurality of serrations disposed along the outer surfaces, a surface coating of plasma sprayed titanium, a plurality of concavities formed by aluminum oxide blasting, one or more fins disposed on each of the outer surfaces and/or the like.

In another aspect of the present invention, an intervertebral disc prosthesis includes a core and upper and lower plates disposed about the core. The core includes upper and lower curved surfaces and at least one resilient material disposed between the upper and lower curved surfaces. Each plate includes an outer surface which engages a vertebra and an inner curved surface shaped to slide over one of the curved surfaces of the core. The resilient material may, as described above, include any suitable material, such as but not limited to a polymer or hydrogel. Generally, the core and plates may include any of the materials or features described above. In some embodiments, one or both of the plates may also include the resilient material included in the core or a different resilient material. Any or all of the core and the plates may further include membranes surrounding the resilient material and/or resilient support structures disposed within the resilient material and connecting separate pieces of the core and/or plates.

In another aspect of the present invention, a method for making an endplate of an intervertebral disc prosthesis involves: forming an outer surface of the endplate, the outer surface adapted to engage a vertebra; forming an inner curved surface of an endplate, the inner curved surface adapted to slide over a curved surface of a core of the disc prosthesis; connecting the outer and inner surfaces with at least one resilient support member disposed between the two; and disposing a resilient material between the outer and inner surfaces to surround the resilient support member(s). In one embodiment, for example, connecting the outer and inner surfaces comprises attaching a plurality of springs between the two surfaces. Disposing the resilient material between the inner and outer surfaces may involve injecting a polymer, hydrogel or any other suitable resilient material. In some embodiments, the resilient material is injected into a cavity formed between the inner and outer endplates. In other embodiments, the resilient material is injected into a retaining structure disposed between the inner and outer endplates. Alternatively, disposing the material between the surfaces may involve placing one or more layers of solid material between them. Optionally, the method may further involve coupling at least one retaining structure with the inner and outer surfaces, around the resilient material, to retain the resilient material between the inner and outer surfaces.

In another aspect of the present invention, a method for making an endplate of an intervertebral disc prosthesis involves: forming an outer surface of the endplate, the outer surface adapted to engage a vertebra; forming an inner curved surface of an endplate, the inner curved surface adapted to slide over a curved surface of a core of the disc prosthesis; disposing a resilient material between the outer and inner surfaces; and coupling the outer surface to the inner surface so as to trap the resilient material between the outer and inner surfaces.

In another aspect of the present invention, a method for making an endplate of an intervertebral disc prosthesis includes: forming an outer surface of the endplate, the outer surface adapted to engage a vertebra and including an inward facing retaining ring; forming an inner curved surface of an endplate, the inner curved surface adapted to slide over a curved surface of a core of the disc prosthesis; disposing a resilient material within the outer surface; disposing the inner surface within the retaining ring of the outer surface to contain the resilient material between the two surfaces; and shrinking at least part of the outer surface to retain the inner surface within the retaining ring. In some embodiments, shrinking the outer surface comprises allowing the outer surface to cool, and the method further comprises heating the outer surface before disposing the inner curved surface within the retaining ring.

These and other aspects and embodiments will be described in further detail below, with reference to the drawing figures.

DETAILED DESCRIPTION OF THE INVENTION

Various embodiments of the present invention generally provide for an intervertebral disc prosthesis having upper and lower plates disposed about a central core. At least one of the plates and/or the core includes a resilient material, which allows the plate(s) and/or core to absorb forces applied to it by vertebrae. Although various embodiments of such a prosthesis are shown in the figures and described further below, the general principles of the present invention, namely including a force absorbing material in the prosthesis, may be applied to any of a number of other disc prostheses, such as but not limited to the LINK® SB Charitédisc (provided by DePuy Spine, Inc.) Mobidisk® (provided by LDR Medical (www.ldmedical.fr)), the Bryan Cervical Disc (provided by Medtronic Sofamor Danek, Inc.), the ProDisc® or ProDisc-C® (from Synthes Stratec, Inc.), and the PCM disc (provided by Cervitech, Inc.).

That being said, FIGS. 1-2 show a prosthetic disc 10 previously described by the assignees of the present invention in U.S. patent application Ser. No. 10/855,253, previously incorporated by reference. Disc 10 for intervertebral insertion between two adjacent spinal vertebrae (not shown) suitably includes an upper plate 12, a lower plate 14 and a core 16 located between the plates. The upper plate 12 includes an outer surface 18 and an inner surface 24 and may be constructed from any suitable metal, alloy or combination of metals or alloys, such as but not limited to cobalt chrome molybdenum, titanium (such as grade 5 titanium), stainless steel and/or the like. In one embodiment, typically used in the lumbar spine, the upper plate 12 is constructed of cobalt chrome molybdenum, and the outer surface 18 is treated with aluminum oxide blasting followed by a titanium plasma spray. In another embodiment, typically used in the cervical spine, the upper plate 12 is constructed of titanium, the inner surface 24 is coated with titanium nitride, and the outer surface 18 is treated with aluminum oxide blasting. An alternative cervical spine embodiment includes no coating on the inner surface 24. In other cervical and lumbar disc embodiments, any other suitable metals or combinations of metals may be used. In some embodiments, it may be useful to couple two materials together to form the inner surface 24 and the outer surface 18. For example, the upper plate 12 may be made of an MRI-compatible material, such as titanium, but may include a harder material, such as cobalt chrome molybdenum, for the inner surface 24. In another embodiment, upper plated 12 may comprise a metal, and inner surface 24 may comprise a ceramic material. All combinations of materials are contemplated within the scope of the present invention. Any suitable technique may be used to couple materials together, such as snap fitting, slip fitting, lamination, interference fitting, use of adhesives, welding and/or the like. Any other suitable combination of materials and coatings may be employed in various embodiments of the invention.

In some embodiments, the outer surface 18 is planar. Oftentimes, the outer surface 18 will include one or more surface features and/or materials to enhance attachment of the prosthesis 10 to vertebral bone. For example, the outer surface 18 may be machined to have serrations 20 or other surface features for promoting adhesion of the upper plate 12 to a vertebra. In the embodiment shown, the serrations 20 extend in mutually orthogonal directions, but other geometries would also be useful. Additionally, the outer surface 18 may be provided with a rough microfinish formed by blasting with aluminum oxide microparticles or the like. In some embodiments, the outer surface may also be titanium plasma sprayed to further enhance attachment of the outer surface 18 to vertebral bone.

The outer surface 18 may also carry an upstanding, vertical fin 22 extending in an anterior-posterior direction. The fin 22 is pierced by transverse holes 23. In alternative embodiments, the fin 22 may be rotated away from the anterior-posterior axis, such as in a lateral-lateral orientation, a posterolateral-anterolateral orientation, or the like. In some embodiments, the fin 22 may extend from the surface 18 at an angle other than 90°. Furthermore, multiple fins 22 may be attached to the surface 18 and/or the fin 22 may have any other suitable configuration, in various embodiments. In other embodiments, the fin 22 In some embodiments, such as discs 10 for cervical insertion, the fins 22, 42 may be omitted altogether.

The inner, spherically curved concave surface 24 is formed at a central (from right to left), axial position with a circular recess 26 as illustrated. At the outer edge of the curved surface 24, the upper plate 12 carries peripheral restraining structure comprising an integral ring structure 26 including an inwardly directed rib or flange 28. The flange 28 forms part of a U-shaped member 30 joined to the major part of the plate by an annular web 32. The flange 28 has an inwardly tapering shape and defines upper and lower surfaces 34 and 36 respectively which are inclined slightly relative to the horizontal when the upper plate 12 is at the orientation seen in FIG. 1. An overhang 38 of the U-shaped member 30 has a vertical dimension that tapers inwardly as illustrated.

The lower plate 14 is similar to the upper plate 12 except for the absence of the peripheral restraining structure 26. Thus, the lower plate 14 has an outer surface 40 which is planar, serrated and microfinished like the outer surface 18 of the upper plate 12. The lower plate 14 optionally carries a fin 42 similar to the fin 22 of the upper plate. The inner surface 44 of the lower plate 14 is concavely, spherically curved with a radius of curvature matching that of the inner surface 24 of the upper plate 12. Once again, this surface may be provided with a titanium nitride or other finish.

At the outer edge of the inner curved surface 44, the lower plate 14 is provided with an inclined ledge formation 46. Alternatively, the lower plate 14 may include peripheral restraining structure analogous to the peripheral restraining structure 26 on the upper plate 12.

The core 16 of the disc 10 may be made out of any suitable polymer. Alternatively, core 16 may be made partially or completely of one or more metals, alloys or a combination of metals or alloys. For further details on a disc 10 with a partially or completely metallic core, reference may be made to U.S. patent application Ser. No. 10/903,913, previously incorporated by reference. For example, metals used to form all or part of the core 16 may include but are not limited to cobalt chrome molybdenum, titanium (such as grade 5 titanium), stainless steel and/or the like. In some embodiments, the core 16 may be made of the same material as the upper plate 12 and the lower plate 14, which may help resist oxidation of metallic surfaces of the disc 10. In alternative embodiments, the core 16 may be made of different material(s) than the plates 12, 14. In the embodiment shown, the core 16 has identical upper and lower spherically curved convex surfaces 48, 50. In some embodiments, the entire core 16 is metallic, while in other embodiments the curved surfaces 48, 50 may be coated or laminated with metal, or one or more metallic surfaces may be otherwise attached to the core 16. In some embodiments, the core 16 is made of a polymer or ceramic, with attached metallic curved surfaces 48, 50. Alternatively, the core 16 may be a hollow metallic structure. The radius of curvature of these surfaces matches the radius of curvature of the inner surfaces 24, 44 of the upper and lower plates 12, 14. The curved surfaces are accordingly complementary.

The core 16 is symmetrical about a central, equatorial plane 52 which bisects it laterally. (Although in other embodiments, the core 16 may be asymmetrical.) Lying on this equatorial plane is an annular recess or groove 54 which extends about the periphery of the core. The groove 54 is defined between upper and lower ribs or lips 56. When the plates 12, 14 and core 16 are assembled and in the orientation seen in FIG. 1, the flange 28 lies on the equatorial plane and directly aligned with the groove 54. The outer diameter 58 of the lips 56 is preferably very slightly larger than the diameter 60 defined by the inner edge of the flange 28. In some embodiments, the core 16 is movably fitted into the upper plate 12 via an interference fit. To form such an interference fit with a metal core 16 and metal plate 12, any suitable techniques may be used. For example, the plate 12 may be heated so that it expands, and the core 16 may be dropped into the plate 12 in the expanded state. When the plate 12 cools and contracts, the interference fit is created. In another embodiment, the upper plate 12 may be formed around the core 16. Alternatively, the core 16 and upper plate 12 may include complementary threads, which allow the core 16 to be screwed into the upper plate 12, where it can then freely move.

In an alternative embodiment (not shown), the outer diameter 58 of the lips 56 may be very slightly smaller than the diameter 60 defined by the inner edge of the flange 28. In such embodiments, the core 16 and the plates 12, 14 are not coupled via an interference fit but are instead coupled via forces applied by the vertebral column itself, thus acting analogously to a ball-and-socket joint.

The central axis of the disc 10 (the axis passing through the centers of curvature of the curved surfaces) is indicated with the reference numeral 62. As shown in FIG. 1, the disc 10 may be symmetrical about a central anterior-posterior plane containing the axis 62. In some embodiments the axis 62 is posteriorly disposed, i.e. is located closer to the posterior limit of the disc than the anterior limit thereof.

In use, the disc 10 is surgically implanted between adjacent spinal vertebrae in place of a damaged disc. The adjacent vertebrae are forcibly separated from one another to provide the necessary space for insertion. The disc 10 is typically, though not necessarily, advanced toward the disc space from an anterolateral or anterior approach and is inserted in a posterior direction—i.e., from anterior to posterior. The disc is inserted into place between the vertebrae with the fins 22, 42 of the plates 12, 14 entering slots cut in the opposing vertebral surfaces to receive them. During and/or after insertion, the vertebrae, facets, adjacent ligaments and soft tissues are allowed to move together to hold the disc in place. The serrated and microfinished surfaces 18, 40 of the plates 12, 14 locate against the opposing vertebrae. The serrations 20 and fins 22, 42 provide initial stability and fixation for the disc 10. With passage of time, enhanced by the titanium surface coating, firm connection between the plates and the vertebrae will be achieved as bone tissue grows over the serrated surface. Bone tissue growth will also take place about the fins 22, 40 and through the transverse holes 23 therein, further enhancing the connection which is achieved.

Figure 4:
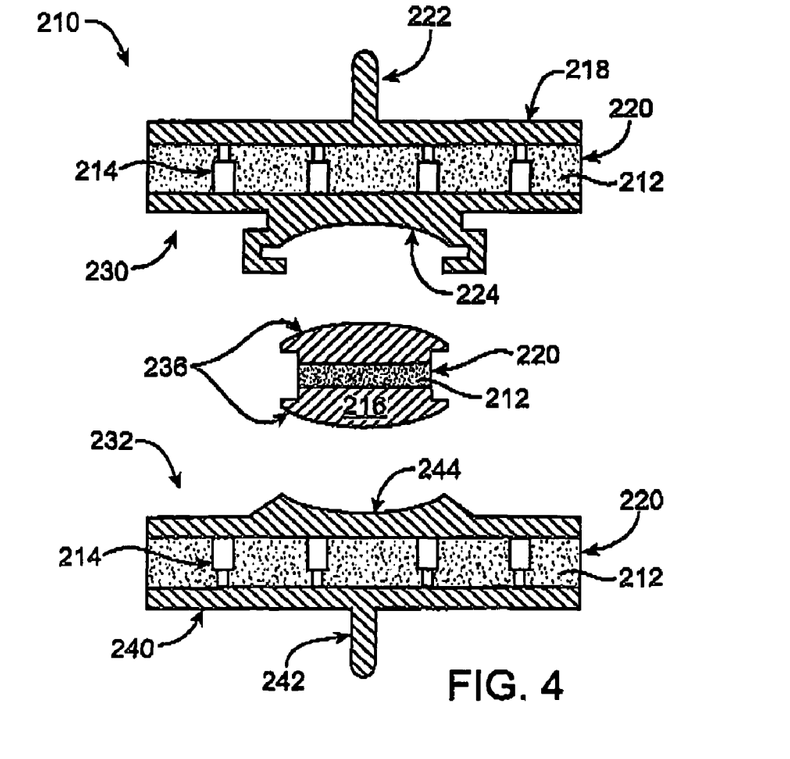
FIG. 4 is a cross-sectional view anterior view of an intervertebral disc prosthesis having shock absorbing endplates and core, according to another embodiment of the present invention.

In the assembled disc 10, the complementary and cooperating spherical surfaces of the plates and core allow the plates to slide or articulate over the core through a fairly large range of angles and in all directions or degrees of freedom, including rotation about the central axis 62. FIGS. 1 and 4 show the disc 10 with the plates 12 and 14 and core 16 aligned vertically with one another on the axis 62. FIG. 2 illustrates a situation where maximum anterior flexion of the disc 10 has taken place. At this position, the upper rib 56 has entered the hollow 38 of the U-shaped member 30, the lower surface of the rib 56 has moved into contact with the upper surface 34 of the flange 28, the flange having moved into the groove 54, and the lower surface 36 of the flange has moved into contact with the upper surface of the ledge formation 46, as will be seen in the encircled areas 69. Abutment between the various surfaces prevents further anterior flexure. The design also allows for the inner extremity of the flange 28 to abut against the base of the groove 54, thereby limiting further relative movement between the core and plate. A similar configuration is achieved in the event of maximum posterior flexure of the plates 12, 14 over the core, such as during spinal extension and/or in the event of maximum lateral flexure.

The flange 28 and the groove 54 defined between the ribs 56, prevent separation of the core from the plates. In other words, the cooperation of the retaining formations ensures that the core is held captive between the plates at all times during flexure of the disc 10.

In an alternative embodiment, the continuous annular flange 28 may be replaced by a retaining formation comprising a number of flange segments which are spaced apart circumferentially. Such an embodiment could include a single, continuous groove 54 as in the illustrated embodiment. Alternatively, a corresponding number of groove-like recesses spaced apart around the periphery of the core could be used, with each flange segment opposing one of the recesses. In another embodiment, the continuous flange or the plurality of flange segments could be replaced by inwardly directed pegs or pins carried by the upper plate 12. This embodiment could include a single, continuous groove 54 or a series of circumferentially spaced recesses with each pin or peg opposing a recess.

In yet another embodiment, the retaining formation(s) could be carried by the lower plate 14 instead of the upper plate, i.e. the plates are reversed. In some embodiments, the upper (or lower) plate is formed with an inwardly facing groove, or circumferentially spaced groove segments, at the edge of its inner, curved surface, and the outer periphery of the core is formed with an outwardly facing flange or with circumferentially spaced flange segments.

Figure 3:
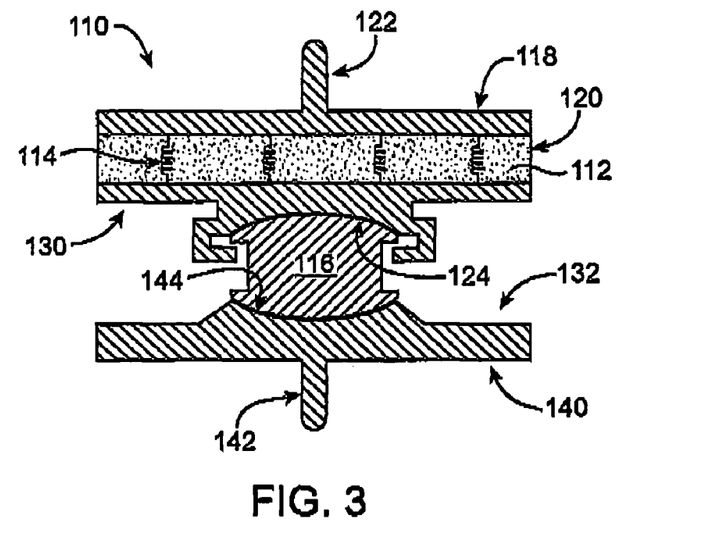
FIG. 3 is a cross-sectional view anterior view of an intervertebral disc prosthesis having shock absorbing endplate, according to one embodiment of the present invention.

Referring now to FIG. 3, one embodiment of an intervertebral prosthetic disc 110 similar to the one shown in FIGS. 1 and 2 but including shock absorbing capabilities is shown. (It should be emphasized that disc 110 of FIG. 3 is not drawn to scale.) Many of the features of disc 110 are analogous to those shown in FIGS. 1-2 and described above, so will not be described again. In the embodiment shown in FIG. 3, prosthetic disc 110 includes two plates 130, 132, each plate having an outer surface 118, 140 that engages a vertebra and includes a fin 122, 142, and an inner curved surface 124, 144 that slides over corresponding curved surfaces of the core 116. Additionally, the "upper" plate 130 (which may actually be upper or lower than the "lower" plate 132, depending on how the disc 110 is disposed between two vertebrae) includes a layer of resilient material 112, with multiple resilient support members 114 disposed throughout the resilient material 112 and connecting the portion of the plate 130 including the outer surface 118 with the portion of the plate including the inner surface 124. A retaining structure 120 surrounds the resilient material to retain it between the outer 118 and inner 124 surface portions of the plate 130.

In various embodiments, upper plate 130, lower plate 132, core 116, or any combination thereof may include one or more resilient materials 112 disposed in a layer or other configuration. Resilient material 112, for example, may be a polymer, hydrogel or other similarly resilient substance. Material 112 may be in liquid, gel or solid form. When in liquid form, resilient material 112 may sometimes be injected into position within one or more plates 130, 132 and/or core 116. When in solid form, one or more layers of solid resilient material 112 may be placed within one or more plates 130, 132 and/or core 116. Resilient support structures 114 may also be made of any suitable material, such as stainless steel, Nitinol™ or the like, and may have any suitable configuration, such as but not limited to springs (as in FIG. 3), wires, cylinders, joints or bands. Any number of support structures 114 may be used. Both resilient material 112 and support structures 114 allow plate 130 to absorb shock or other forces applied to it by vertebrae. Surrounding resilient material 112 is the retaining structure 120, which in various embodiments may be a membrane, mesh or the like, made of any material capable of retaining the resilient material 112 while also allowing for shock absorption.

Referring now to FIG. 4, an alternative embodiment of an intervertebral disc prosthesis 210 includes two plates 230, 232, each plate having an outer surface 218, 240 that engages a vertebra and includes a fin 222, 242, and an inner curved surface 224, 244 that slides over corresponding curved surfaces of the core 216. Additionally, each of the "upper" plate 230, the lower plate 232 and the core 216 includes a layer of resilient material 212. The plates 230, 232 further include multiple resilient support members 214 disposed throughout the resilient material 212 and connecting the portion of each plate 230, 232 including the outer surface 218, 240 with the portion of each plate 230, 232 including the inner surface 124, 224, 244. A retaining structure 220 surrounds each layer of resilient material 212 to retain it within the plate 230, 232 or core 216.

Figure 4A:
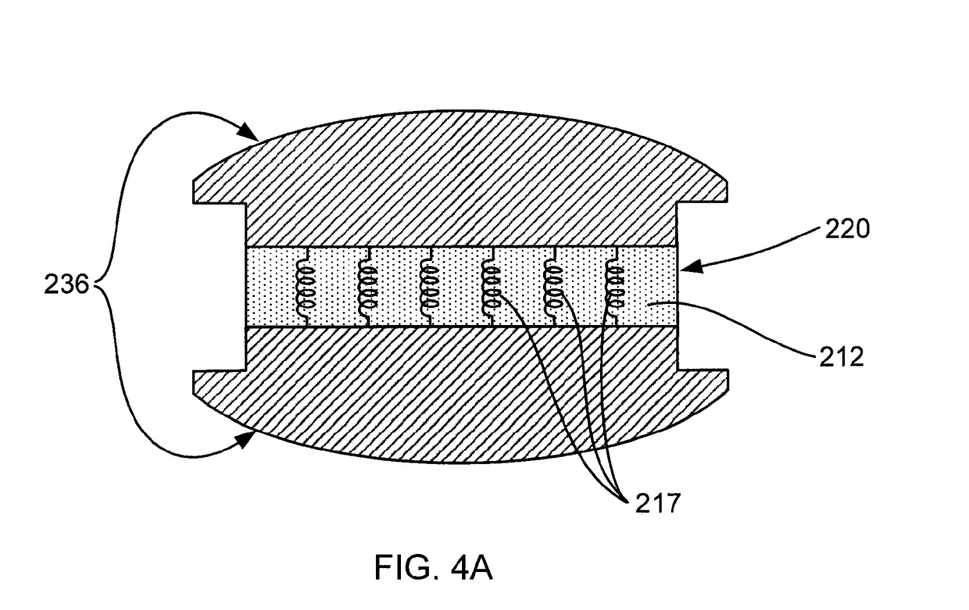
FIG. 4A illustrates a plurality of springs in the core between the endplates.

In the embodiment shown, resilient support members 214 are cylinders, which in some embodiments may each surround a spring. Core 216 includes two curved surfaces 236 with resilient material 212 disposed between them and held together by retaining structure 220. In an alternative embodiment, core 216 may also include resilient support structures, such as a plurality of springs 217 as shown in FIG. 4A. In some embodiments, the resilient material 212 may be injected into its position in the plates 230, 232 and core 216, through the retaining structure 220.

Figure 5:
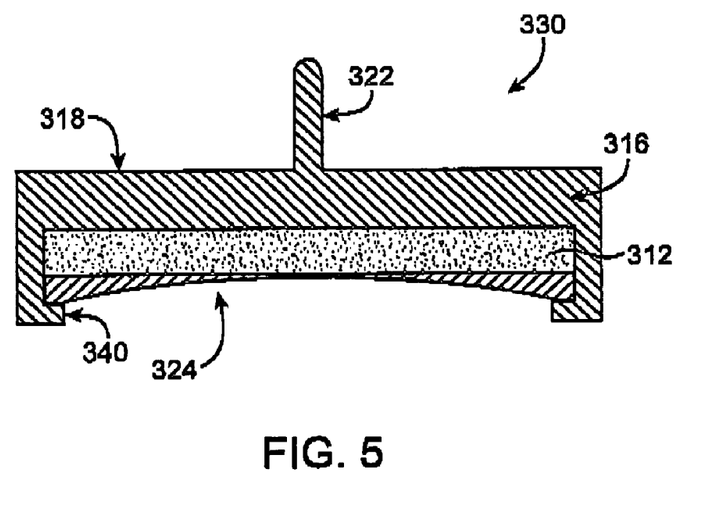
FIG. 5 is a cross-sectional view of an endplate of an intervertebral disc prosthesis, according to one embodiment of the present invention.

With reference now to FIG. 5, one embodiment of a plate 330 of an intervertebral disc includes an outer portion 316, having an outer surface 318, a fin 322 and an inward-facing retaining ring 340, an inner curved surface portion 324, and resilient material 312 disposed between the outer portion 316 and the inner curved surface portion 324. Plate 330 is constructed by disposing resilient material 312 within outer portion 316, disposing curved inner portion 324 within retaining ring 340, and shrinking outer portion 316 to retain inner portion 324 within retaining ring 340. For example, outer portion 316 may be heated, causing it to expand and thus allowing inner portion to fit through retaining ring 340, and then outer portion 316 is allowed to cool, thus shrinking and locking inner portion 324 within retaining ring 340. The resilient material 312 is thus retained between outer portion 316 and inner portion 324. Additionally, inner curved portion 324 is free to move up and down within outer portion 316, according to the resiliency of the resilient material 312, thus providing the shock absorbing capabilities. At the same time, retaining ring 340 prevents the curved inner surface from separating from outer portion 316. In an alternative embodiment, inner curved portion 324 may be cooled to cause it to shrink and may then be positioned within outer portion 316, thus not requiring heating of outer portion 316.

Figure 6:
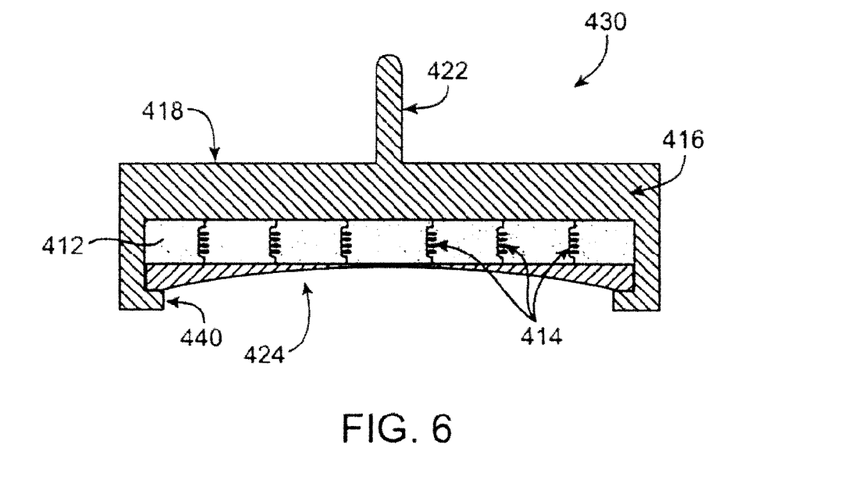
FIG. 6 is a cross-sectional view of an endplate of an intervertebral disc prosthesis, according to another embodiment of the present invention.

Referring now to FIG. 6, an alternative embodiment of a plate 430 of an intervertebral disc includes an outer portion 416, having an outer surface 418, a fin 422 and an inward-facing retaining ring 440, an inner curved surface portion 424, and resilient material 412 disposed between the outer portion 416 and the inner curved surface portion 424. In this embodiment, outer portion 416 is coupled with inner portion 424 via multiple resilient support members 414. Although shown as springs in FIG. 6, in alternative embodiments, resilient support members 414 may comprise cylinders, springs surrounded by cylinders, Nitinol wires, or the like, as described in greater detail above. Aside from resilient support members, plate 430 is constructed in much the same manner as the plate 330 in FIG. 5. The density and amount of resilient material 412 used, the number and stiffness of resilient support members 414 used and/or the height of plate 430 may all be changed in various embodiments of plate 430 to select a desired amount of shock absorption.

Although the foregoing is a complete and accurate description of the invention, any of a number of modifications, additions or the like may be made to the various embodiments without departing from the scope of the invention. Therefore, nothing described above should be interpreted as limiting the scope of the invention at it is described in the claims.

What is claimed is:

1. An intervertebral disc prosthesis comprising:
   a core comprising:

upper and lower curved surfaces; and
at least one shock absorbing element disposed between the upper and lower curved surfaces, wherein the shock absorbing element comprises at least one resilient support member disposed between the upper and lower curved surfaces, and wherein the at least one resilient support member comprises a plurality of springs at least one of which is positioned within the at least one resilient support member; and
upper and lower plates disposed about the core, each plate comprising:
an outer surface which engages a vertebra; and
an inner curved surface corresponding in shape to the curved surfaces of the core and configured to slide over one of the curved surfaces of the core.

2. A disc prosthesis as in claim 1, wherein the at least one shock absorbing element comprises a polymer.

3. A disc prosthesis as in claim 1, wherein the at least one shock absorbing element comprises a hydrogel.

4. A disc prosthesis as in claim 1, wherein the upper and lower curved surfaces of the core comprise a material selected from the group consisting of a polymer, a ceramic and a metal.

5. A disc prosthesis as in claim 4, wherein the metal is selected from the group consisting of cobalt chrome molybdenum, titanium and stainless steel.

6. A disc prosthesis as in claim 1, wherein an additional shock absorbing element is disposed between the outer and inner surfaces of at least one of the upper and lower plates.

7. A disc prosthesis as in claim 6, wherein the additional shock absorbing element is disposed between the outer and inner surface of each plate.

8. A disc prosthesis as in claim 7, further comprising at least one resilient support member disposed within the additional shock absorbing elements and attached to the inner and outer surfaces of each plate.

9. A disc prosthesis as in claim 8, wherein the at least one resilient support member comprises a plurality of springs.

10. A disc prosthesis as in claim 1, wherein the resilient support member is formed of Nitinol.

11. A disc prosthesis as in claim 1, wherein the upper and lower curved surfaces of the core are formed from a rigid material.

12. A disc prosthesis as in claim 11, wherein the upper and lower rigid curved surfaces of the core slide over the inner curved surfaces of the upper and lower plates allowing the core to both rotate and translate with respect to each of the upper and lower plates.

13. A disc prosthesis as in claim 1, wherein the shock absorbing element comprises a resilient material injected between the upper and lower curved surfaces of the core.

14. A disc prosthesis as in claim 1, further comprising a retaining structure which surrounds the shock absorbing element to retain the shock absorbing element in the core.

15. A disc prosthesis as in claim 1, wherein the core both translates and rotates with respect to each of the upper and lower plates.

16. An intervertebral disc prosthesis comprising:
a first plate having an outer surface which engages a vertebra and an inner curved bearing surface;
a second plate having an outer surface which engages a vertebra and an inner bearing surface;
a core having upper and lower rigid surfaces corresponding in shape to the inner surfaces of the first and second plates, wherein the upper and lower rigid surfaces of the core are configured to cooperate with and slide over the inner bearing surfaces of the first and second plates; and
at least one shock absorbing element disposed between the upper and lower surfaces of the core and arranged to provide shock absorption of forces applied to adjacent vertebrae, wherein the shock absorbing element comprises a plurality of springs between the upper and lower curved surfaces of the core at least one of which springs is positioned within the at least one shock absorbing element.

17. A disc prosthesis as in claim 16, wherein the shock absorbing element comprises a resilient material between the upper and lower curved surfaces of the core.

18. An intervertebral disc prosthesis comprising:
a core comprising:
upper and lower members; and
at least one shock absorbing element disposed between the upper and lower members, wherein the shock absorbing element comprises at least one resilient support member disposed between the upper and lower members, and wherein the at least one resilient support member comprises a plurality of coil springs extending from the upper member to the lower member; and
upper and lower plates disposed about the core, each plate comprising:
an outer surface which engages a vertebra; and
an inner curved surface corresponding in shape to and configured to slide one outer bearing surface of the upper or lower member of the core.

* * * * *